United States Patent [19]
Dexter et al.

[11] Patent Number: 6,022,501
[45] Date of Patent: Feb. 8, 2000

[54] PH-SENSITIVE MICROCAPSULES

[75] Inventors: Robin William Dexter, Yardley, Pa.; Brian Eric Benoff, Hawthorne, N.J.

[73] Assignee: American Cyanamid Company, Madison, N.J.

[21] Appl. No.: 08/702,088

[22] Filed: Aug. 15, 1996

[51] Int. Cl.[7] .............................. B01J 13/14; B01J 13/16
[52] U.S. Cl. .......................... 264/4.7; 424/405; 424/408; 424/419; 424/497
[58] Field of Search .............................. 264/4.7; 424/405, 424/408, 419, 497

[56] References Cited

U.S. PATENT DOCUMENTS

| | | | |
|---|---|---|---|
| 3,429,827 | 2/1969 | Ruus | 264/4.7 |
| 3,577,515 | 5/1971 | Vandegaer . | |
| 4,360,376 | 11/1982 | Koestler . | |
| 4,563,212 | 1/1986 | Becher et al. . | |
| 4,956,129 | 9/1990 | Scher et al. . | |
| 5,120,349 | 6/1992 | Stewart . | |

FOREIGN PATENT DOCUMENTS

| | | |
|---|---|---|
| 0093668 | 5/1982 | European Pat. Off. . |
| 2280164A | 12/1995 | United Kingdom . |
| WO93/18853 | 9/1993 | WIPO . |
| WO94/13139 | 6/1994 | WIPO . |

OTHER PUBLICATIONS

Kokufuta, E., et al, 1988, Preparation of polyelectrolyte–coated pH–sensitive poly(styrene) microcapsules and their application to initiation–cessation control of an enzyme reaction, *Biotechnology and Bioengineering*, 32, 289–294.

Miyauchi, E., et al., 1992, "Dependence on pH of permeability towards electrolyte ions of poly(L–lysine–alt–terephthalic acid) microcapsule membranes", *Journal of Microencapsulation*, 9, 329–333.

Miyauchi, E., et al, 1992, "Dependence on pH of permeability towards electrolyte ions of poly(L–lysine–alt–terephthalic acid) microcapsule membranes", *Journal of Microencapsulation*, 9, 329–333.

Khare, A. R. and Peppas, N. A., 1991, "The structure and transport properties of enviromentally sensitive hydrogels", *Polymer News*, 16, (8), 230–236.

*Primary Examiner*—Jeffrey C. Mullis
*Attorney, Agent, or Firm*—Timothy J. Babcock

[57] ABSTRACT

The present invention provides pH-sensitive microcapsules, compositions containing them, methods for their preparation and methods for their use.

10 Claims, 3 Drawing Sheets

PH-SENSITIVE MICROCAPSULES

BACKGROUND OF THE INVENTION

Microencapsulation is a well known method used to formulate water-immiscible materials. Microcapsules are usually designed to prevent their active ingredients from permeating the capsule wall during the storage period before use. For example, the active ingredient present in microcapsules which are formulated as a suspension concentrate may leak from the capsules during storage and cause undesirable changes in the toxicological properties and/or physical properties of the suspension. In particular, active ingredient leakage may effect the flow, viscosity and appearance of the suspension, and lead to crystal growth. Crystal growth is especially problematic because it increases the viscosity of the suspension, causes sediment formation in the suspension and may cause blockages in the equipment used to distribute the suspension.

In the past, thick walled microcapsules have been used to prevent permeation of water-immiscible active ingredients. However, thick walled microcapsules are not entirely satisfactory because they do not readily and/or completely release their active ingredients when used for their intended purpose.

Certain pH-sensitive poly(styrene) microcapsules are described by Kokufuta, et al in Biotechnology and Bioengineering, 32, 289–294 (1988). That paper discloses that poly(styrene) microcapsules are coated with a polyelectrolyte to make them pH sensitive. However, water-immiscible materials cannot be encapsulated by the process described by Kokufuta, et al.

Poly(L-lysine-alt-terephthalic acid) microcapsules which exhibit pH dependence are described by Miyauchi, et al, in Journal of Microencapsulation, 9 (3), 329–333 (1992). However, that paper only describes the preparation of water-containing microcapsules and does not disclose a method for the preparation of microcapsules containing a water-immiscible material.

It is, therefore, an object of the present invention to provide microcapsules which contain water-immiscible materials and rapidly release their contents when used for their intended purpose.

It is also an object of the present invention to provide storage stable, aqueous microcapsule compositions which do not readily crystallize.

Those and other objects of the present invention will become more apparent from the detailed description thereof set forth below.

SUMMARY OF THE INVENTION

The present invention provides pH-sensitive microcapsules which comprise a water-immiscible active ingredient within a shell wall wherein said shell wall has free carboxylic acid groups incorporated therein.

The present invention also relates to the pesticidal use of those microcapsules, compositions containing those microcapsules and a method for the preparation of those microcapsules.

DETAILED DESCRIPTION OF THE INVENTION

The present invention provides a pH-sensitive microcapsule which comprises a water-immiscible active ingredient within a shell wall wherein said shell wall has free carboxylic acid groups incorporated therein.

The microcapsules of the present invention are termed "pH-sensitive" because of their unique dependence on the pH of the environment they are in. Advantageously, it has been found that microcapsules having free carboxylic acid groups incorporated into their shell walls are stable at pH values from about pH 1 to pH 5.5 and release their contents at pH values greater than about 5.5.

Uniquely, the pH-sensitive microcapsules of the present invention may be stored at pH values from about pH 1 to pH 5.5 for extended periods of time without the problems associated with conventional formulations such as crystallization and sedimentation. In addition, the microcapsules of the present invention readily release their contents when exposed to an environment having a pH of greater than about 5.5. In contrast, conventional microcapsules, which are designed for improved storage stability, do not readily and/or completely release their contents when used for their intended purpose.

Shell walls suitable for use in the present invention include any conventional shell walls capable of having free carboxylic acid groups incorporated therein. Preferably, the shell wall is a polyamide, a polyester, a polyamide/polyester copolymer or a cross-linked amino resin each having free carboxylic acid groups incorporated therein.

In a preferred embodiment of the present invention, the polyamide shell wall having free carboxylic acid groups incorporated therein is formed from a polyacid halide and a polyamine, the polyester shell wall having free carboxylic acid groups incorporated therein is formed from a polyacid halide and a polyol, the polyamide/polyester shell wall having free carboxylic acid groups incorporated therein is formed from a polyacid halide, a polyamine and a polyol, and the cross-linked amino resin shell wall having free carboxylic acid groups incorporated therein is formed from a polyacid halide and a water-immiscible amino resin prepolymer.

To ensure that the polyamide, polyester and polyamide/polyester shell walls have free carboxylic acid groups incorporated therein, the ratio of acid halide groups to amino and/or hydroxy groups in the shell wall forming materials is preferably greater than 1:1 and less than about 5:1, more preferably about 2:1 to 3:1. And to ensure that the cross-linked amino resin shell wall has free carboxylic acid groups incorporated therein, the ratio of the water-immiscible amino resin prepolymer to polyacid halide is preferably about 20:1 to 5:1 on a weight basis.

The discovery of the pH-sensitive microcapsules of the present invention, which incorporate free carboxylic acid groups in a polyamide, polyester or polyamide/polyester shell wall, is especially unexpected in view of the state of the microencapsulation art. The principles of interfacial polymerization used to encapsulate water-immiscible materials are well known in the art (see, for example, U.S. Pat. No. 3,577,515; U.S. Pat. No. 4,360,376 and U.S. Pat. No. 4,563,212). Those patents disclose the use of at least a stoichiometric amount of amino and/or hydroxy groups to acid halide groups and further disclose that the ratio of amino and/or hydroxy groups to acid halide groups is preferably greater than 1:1. However, when an equivalent or excess amount of amino and/or hydroxy groups are used, as required in those patents, free carboxylic acid groups are not produced.

The pH-sensitive microcapsules of the present invention which incorporate free carboxylic acid groups in a cross-linked amino resin shell wall are particularly surprising in view of U.S. Pat. No. 4,956,129. U.S. Pat. No. 4,956,129 describes the preparation of microcapsules having a cross-linked amino resin shell wall which is formed from a water-immiscible etherified urea-formaldehyde prepolymer. However, microcapsules prepared by the process of that patent do not exhibit pH-sensitivity. In fact, that patent teaches that it is preferable to raise the pH of an aqueous microcapsule composition once the shell wall is formed by adding any water-soluble base.

The pH-sensitivity of the microcapsules of the present invention makes them especially suitable for use in agricultural applications. The microcapsules may be stored in aqueous compositions having a low pH for several months without any significant degradation. Those stable compositions may then be diluted with water and sprayed onto soil. Because the pH of soil is generally greater than 5.5, the microcapsules of the present invention will release their contents significantly faster and/or more completely than microcapsules which do not incorporate free carboxylic acid groups in their shell walls.

Polyacid halides suitable for use in the present invention include conventional polyacid halides such as triacid halides and diacid halides. Preferred polyacid halides are triacid chlorides, triacid bromides, diacid chlorides and diacid bromides. Triacid chlorides such as trimesoyl chloride, trimer acid chloride and the like, and diacid chlorides such as terephthaloyl chloride, sebacoyl chloride, adipoyl chloride, azelaoyl chloride, dodecanedioic acid chloride, dimer acid chloride and the like are more preferred. In addition, polyacid halide equivalents may also be used in shell wall forming reactions.

Polyamines suitable for use in the present invention include conventional polyamines such as diamines and triamines. Diamines such as 1,6-hexamethylenediamine, ethylenediamine, 1,3-pentanediamine, 2-methylpentamethylenediamine, propylene-1,3-diamine, tetramethylenediamine, pentamethylenediamine, 4,9-dioxadodecane-1,12-diamine, 1,3-phenylenediamine, 2,4- and 2,6-toluene-diamine, 4,4'-diaminodiphenylmethane and the like, and triamines such as diethylenetriamine, 1,3,5-benzenetriamine, 2,4,6-triaminotoluene and the like are suitable for use in this invention with diamines being preferred. Hydrochloride salts of those polyamines may also be used to form the polyamide shell wall having free carboxylic acid groups.

Polyols which are suitable for use include conventional polyols such as diols and triols. Preferred polyols include glycols such as ethylene glycol, propylene glycol, hexylene glycol, diethylene glycol, triethylene glycol and the like, bisphenol A, hydroquinone, resorcinol, catechol, pyrogallol, phloroglucinol dihydrate, pentaerythritol, trimethylolpropane, and the like with ethylene glycol being more preferred.

Water-immiscible amino resin prepolymers suitable for use in the present invention include conventional water-immiscible amino resin prepolymers such as partially etherified urea-formaldehyde prepolymers, partially etherified melamine-formaldehyde prepolymers and the like and mixtures thereof with partially etherified urea-formaldehyde prepolymers being preferred. Partially etherified urea-formaldehyde and melamine-formaldehyde prepolymers are urea-formaldehyde and melamine-formaldehyde prepolymers, respectively, wherein about 50% to 98% of the hydroxyl hydrogen atoms of the methylol groups of the corresponding urea- and melamine-formaldehyde prepolymers are replaced with $C_4$–$C_{10}$ alkyl groups. In a preferred embodiment of the present invention, about 60% to 90% of the methylol groups of the urea- and melamine-formaldehyde prepolymers are etherified with n-butanol. A further description of etherified urea-formaldehyde prepolymers and methods for their preparation is presented in U.S. Pat. No. 4,956,129.

In general, any water-immiscible active ingredient which has a melting point below about 100° C. or is soluble in a water-immiscible solvent and is compatible with the shell wall forming materials may be used in the present invention. The pH-sensitive microcapsules of the present invention preferably contain water-immiscible agricultural compounds such as herbicides, insecticides, acaricides, nematicides, fungicides, molluscicides, plant growth regulators, safeners, algicides, mildewicides, ectoparasiticides and the like and combinations thereof. Herbicides, insecticides, acaricides, nematicides, fungicides and molluscicides are preferred. Herbicidal compounds especially suitable for use in the present invention include dinitroaniline compounds such as pendimethalin and trifluralin, and haloacetanilide compounds such as alachlor, metolachlor and propachlor. Insecticidal compounds especially suitable for use in the present invention include phosphoric acid ester compounds such as terbufos, malathion, chlorpyrifos, diazinon and profenofos, and pyrethroid compounds such as cypermethrin, alpha-cypermethrin and permethrin.

The pH-sensitive microcapsules of the present invention typically have a median diameter of about 1 micrometer to 200 micrometers, preferably about 3 micrometers to 50 micrometers, and more preferably about 5 to 15 micrometers.

The present invention also relates to an improved process to make aqueous microcapsules containing a water-immiscible active ingredient having a polyamide, polyester, polyamide/polyester or a cross-linked amino resin shell wall, the improvement which comprises incorporating free carboxylic acid groups in said shell wall by adding excess polyacid halide during shell wall formation.

By excess polyacid halide it is meant an amount over a conventional process: (1) in the case of a polyamide, polyester or polyamide/polyester shell wall the ratio of acid halide groups to amino and/or hydroxy groups present in the shell wall forming materials should be greater than 1:1 and less than about 5:1 in accordance with the present invention whereas conventional processes use less polyacid halide; and (2) in the case of a cross-linked amino resin shell wall where polyacid halides are not conventionally added, the present invention contemplates the use of polyacid halide such that the ratio of the amino resin prepolymer shell wall forming material to polyacid halide in the present invention is preferably about 20:1 to 5:1 on a weight basis.

Advantageously the process of the present invention may be carried out at conventional temperatures. Of course, the temperature depends on the type of shell wall being formed. When forming a polyamide, polyester, polyamide/polyester shell wall the process is generally conducted at an elevated temperature to maintain the water-immiscible active ingredient in a liquid state, and to enhance the wall forming reaction rate; the process is preferably conducted at a temperature of about 35° C. to 85° C. and is more preferably conducted at a temperature of about 50° C. to 65° C. When forming a cross-linked amino resin shell wall, the emulsion is conventionally heated to about 50° C. to 100° C. to ensure formation of the shell wall; this temperature (preferably 60° to 80° C.) also enables the polyacid halide and amino resin prepolymer react and form the cross-linked amino resin shell wall having free carboxylic acid groups incorporated therein.

In a preferred embodiment the process of the invention, the pH of the aqueous, pH-sensitive microcapsule composition is about pH 1 to pH 5.5, preferably about pH 2 to pH 4. To ensure that the aqueous, pH-sensitive microcapsule compositions are in the desired pH range, a base or mixture of bases may be added during or after shell wall formation. Bases suitable for use in this invention include alkali metal hydroxides such as sodium hydroxide and potassium hydroxide and alkali metal carbonates such as sodium carbonate and potassium carbonate. Sodium hydroxide is the preferred base.

Various shell wall thicknesses can be achieved in accordance with the invention. In general, wall thickness would be selected relative to the desired application for the microcapsule. When forming shell walls made of polyamide, polyester or polyamide/polyester, the water-immiscible solution preferably contains about 1% to 15%, more preferably about 2% to 8%, by weight of the polyacid halide, and the polyamine, polyol or mixture thereof is preferably present in an amount from about 0.3% to 5%, more preferably from about 0.6% to 3%, by weight relative to that of the water-immiscible solution. When forming a cross-linked amino resin shell wall, the water-immiscible solution preferably contains about 1% to 3% by weight of the polyacid halide and about 5% to 20% by weight of the amino resin prepolymer.

Advantageously, the pH-sensitive microcapsules may be prepared using any conventional emulsifier. In particular, emulsifiers such as polyvinyl alcohols, alkylated vinylpyrrolidone polymers, ethoxylated lignosulfonic acid salts, lignosulfonic acid salts, oxidized lignins, lignin salts, salts of styrene-maleic anhydride copolymers, salts of partial esters of styrene-maleic anhydride copolymers, partial salts of polyacrylic acid, partial salts of polyacrylic acid terpolymers and the like and mixtures thereof are suitable for use in the processes of this invention. In the above described emulsifiers, sodium, potassium, magnesium, calcium and ammonium salts are generally preferred with sodium and magnesium salts being particularly preferred. Preferred emulsifiers for use in the processes of this invention include polyvinyl alcohols, alkylated vinylpyrrolidone polymers, and lignosulfonic acid salts.

The aqueous solutions used in the process of this invention preferably contain about 0.5% to 5%, more preferably about 1% to 3%, by weight of the emulsifier or mixture of emulsifiers. The aqueous, pH-sensitive microcapsule compositions prepared by the process of this invention preferably contain about 5% to 60%, more preferably about 20% to 50%, by weight of the water-immiscible active ingredient.

The water-immiscible solutions used in the process of this invention are prepared by mixing a polyacid halide and, if necessary, an amino resin prepolymer with an active ingredient at a temperature above the melting point of the active ingredient, provided that the temperature is below the temperature required to initiate the wall forming reactions if an amino resin prepolymer is used. Alternatively, the water-immiscible solution may be prepared by mixing a polyacid halide and, if employed, an amino resin prepolymer with a solution of an active ingredient in a suitable water-immiscible solvent.

Water-immiscible solvents which are suitable for use include solvents which do not react undesirably with any of the ingredients used in the invention processes. Suitable solvents include water-immiscible hydrocarbons, aromatic hydrocarbons, halogenated hydrocarbons, halogenated aromatic hydrocarbons, ketones, long chain esters and mixtures thereof.

More particularly the present invention provides a process for the preparation of an aqueous, pH-sensitive microcapsule composition having free carboxylic acid groups incorporated in a cross-linked amino resin shell wall which process comprises:

(a) providing an aqueous solution containing an emulsifier;

(b) dispersing, with agitation, in the aqueous solution, a water-immiscible solution comprising a water-1immiscible amino resin prepolymer, a polyacid halide, and a water-immiscible active ingredient to form an emulsion, preferably the ratio of amino resin prepolymer to polyacid halide is about 20:1 to 5:1 on a weight basis; and (c) heating the emulsion to about 50° C. to 100° C.

In a preferred embodiment of the present invention, the amino resin prepolymer is an etherified urea-formaldehyde prepolymer provided in the form of a solution in alcohol or a mixture in alcohol and xylene. In general, the alcohol used in those solutions and mixtures is the same as the alcohol used to etherify the corresponding urea-formaldehyde prepolymer.

In another particular embodiment, the present invention also relates to a preferred process, i.e. the preparation of an aqueous, pH-sensitive microcapsule composition having free carboxylic acid groups incorporated in a polyamide, polyester or polyamide/polyester shell wall which process comprises:

(a) providing an aqueous solution comprising an emulsifier;

(b) dispersing, with agitation, in the aqueous solution, a water-immiscible solution comprising a polyacid halide and a water-immiscible active ingredient to form an emulsion; and (c) adding, with agitation, to the emulsion of step (b), a polyamine, a polyol or a mixture thereof, provided that the ratio of acid halide groups to amino and/or hydroxy groups is greater than 1:1 and less than about 5:1.

When forming polyamide, polyester or polyamide/polyester shell walls in accordance with the process of this invention, the ratio of acid halide groups to amino and/or hydroxy groups is an especially important feature because it ensures that the microcapsule shell wall contains free carboxylic acid groups. In a preferred embodiment, the ratio of acid halide groups to amino and/or hydroxy groups in the shell wall forming materials is about 2:1 to 3:1.

Additional wall forming materials such as polyisocyanates, polychloroformates and polysulfonyl chlorides, which react with polyamines and polyols, may be added to the water-immiscible solution of this preferred process. Those additional wall forming materials are added in amounts such that they do not prevent the formation of free carboxylic acid groups in the shell wall.

This invention further provides an aqueous, pH-sensitive microcapsule composition which comprises a water-immiscible active ingredient within a shell wall, wherein said shell wall has free carboxylic acid groups incorporated therein, suspended in an aqueous solution having a pH of about pH 1 to pH 5.5.

To obtain a storage stable, aqueous, pH-sensitive microcapsule composition, the pH of the composition is preferably lower than about pH 4 to prevent premature release of the water-immiscible material. In a preferred embodiment of the present invention, the pH of the aqueous, pH-sensitive microcapsule composition is about pH 2 to pH 4.

This invention also provides a method for controlling pests such as weeds, insects, acarina, fungi, nematodes and the like by applying to the locus of the pest a pesticidally effective amount of a microencapsulated pesticide which comprises a water-immiscible pesticide within a shell wall wherein said shell wall has free carboxylic acid groups incorporated therein. In particular, this invention provides a method for controlling undesirable plant species which comprises applying to the foliage of the plants or to the soil or water containing seeds or other propagating organs thereof, a herbicidally effective amount of a microencapsulated herbicide which comprises a water-immiscible herbicide within a shell wall wherein said shell wall has free carboxylic acid groups incorporated therein.

The present invention also provides pesticidal compositions comprising an agronomically acceptable inert solid or liquid carrier and a pesticidally effective amount of a microencapsulated pesticide which comprises a water-immiscible pesticide within a shell wall wherein said shell wall has free carboxylic acid groups incorporated therein. Advantageously, the aqueous, pH-sensitive microcapsule compositions of this invention may be used directly as pesticidal compositions and are diluted with water for use. Alternatively, additional ingredients such as antisettling agents, salts, antifoams, surfactants, pH-adjustors, antifreeze agents and the like may be added to the aqueous, pH-sensitive microcapsule compositions of the present invention. The pesticidal compositions of this invention preferably have a pH of about pH 2 to pH 4.

In order to facilitate a further understanding of the invention, the following examples are presented primarily for the purpose of illustrating more specific details thereof. The invention should not be deemed limited by the examples as the full scope of the invention is defined in the claims.

EXAMPLE 1

Preparation of pH-sensitive microcapsule compositions using trimesoyl chloride, 1,6-hexamethylenediamine and polyvinyl alcohol A mixture of pendimethalin (70.0 g), trimesoyl chloride (5.0 g) and AROMATIC®200, an aromatic hydrocarbon mixture ($C_{10}$ to $C_{13}$ aromatics, distillation range 226°–279° C.), EXXON Corp., Houston, Tex. (85.0 g) is stirred at 60° C. to obtain a water-immiscible solution. The water-immiscible solution is added with stirring to a polyvinyl alcohol solution (120.0 g of a 2 wt/wt % solution) at 60° C. to obtain an emulsion. Thereafter, the stirrer speed is reduced and a solution of 1,6-hexamethylenediamine (HMDA, 2.2 g of a 50 wt/wt % solution), sodium hydroxide (1.8 g of a 50 wt/wt % solution) and water (31.0 g) is added to the stirred emulsion and the resultant mixture is stirred at 60° C. for about 4 hours to form the pH-sensitive microcapsule composition identified as composition number 1 in Table I.

Using essentially the same procedure, the pH-sensitive microcapsule compositions identified as composition numbers 2–12 in Table I are obtained.

TABLE I pH-Sensitive Microcapsule Compositions

Ingredient/wt/wt %

| Composition Number | Pendimethalin | Trimesoyl Chloride | HMDA | NaOH | Polyvinyl Alcohol | AROMATIC ® 200 | Total Water |
| --- | --- | --- | --- | --- | --- | --- | --- |
| 1 | 22.22 | 1.59 | 0.35 | 0.29 | 0.76 | 26.98 | 47.81 |
| 2 | 22.22 | 1.59 | 0.52 | 0.29 | 0.76 | 26.98 | 47.63 |
| 3 | 22.22 | 0.79 | 0.17 | 0.14 | 0.76 | 27.78 | 48.13 |
| 4 | 22.22 | 2.38 | 0.52 | 0.43 | 0.76 | 26.19 | 47.49 |
| 5 | 22.22 | 3.17 | 0.70 | 0.57 | 0.76 | 25.40 | 47.17 |
| 6 | 22.22 | 1.59 | 0.48 | 0.29 | 0.76 | 26.98 | 47.68 |
| 7 | 39.68 | 1.59 | 0.48 | 0.29 | 0.76 | 9.52 | 47.68 |
| 8 | 44.44 | 1.59 | 0.48 | 0.29 | 0.76 | 4.76 | 47.68 |
| 9 | 22.22 | 1.59 | 0.48 | 0.00 | 0.76 | 26.98 | 47.96 |
| 10 | 22.40 | 2.40 | 0.53 | 0.43 | 0.77 | 26.40 | 47.07 |
| 11 | 41.18 | 3.24 | 0.71 | 0.58 | 0.82 | 8.82 | 44.65 |
| 12 | 41.18 | 3.24 | 1.42 | 0.58 | 0.82 | 8.82 | 43.94 |

EXAMPLE 2

Preparation of pH-sensitive microcapsule compositions using Beetle 1050® resin and trimesoyl chloride A mixture of pendimethalin (110.0 g), Beetle 1050® resin[1] (20.0 g), trimesoyl chloride (2.5 g) and AROMATIC® 200[2] (30.0 g) is stirred at 55° C. to obtain a water-immiscible solution. The water-immiscible solution is added with stirring to an aqueous solution of 120 g of a 2 wt/wt % AIRVOL® 205[3] solution and 10.0 g of a 20 wt/wt % REAX®88B[4] solution at 65° C. to obtain an emulsion. The emulsion is stirred for one hour while the temperature is slowly increased to 70° C. Additional water (50.0 g) is added and the emulsion is stirred at 70° C. for one hour and allowed to cool to room temperature to obtain the pH-sensitive microcapsule composition identified as composition number 13 in Table II.

[1] A butylated urea-formaldehyde resin in xylene and n-butanol, Cytec Industries, West Paterson, N.J.
[2] Aromatic hydrocarbon mixture ($C_{10}$ to $C_{13}$ aromatics, distillation range 226°–279° C.), Exxon Corp., Houston, Tex.
[3] A partially hydrolyzed vinyl acetate polymer, Air Products and Chemicals Inc., Allentown, Pa.
[4] Sodium salt of lignosulfonic acid, Westvaco, Charleston Heights, S.C.

Using essentially the same procedure, the pH-sensitive microcapsule compositions identified as composition numbers 14-19 in Table II are obtained.

TABLE II pH-Sensitive Microcapsule Compositions

Ingredient/wt/wt %

| Comp. No. | Pendimethalin | Beetle 1050 ® Resin | Trimesoyl Chloride | AIRVOL ® 205 | REAX ® 88B | AROMATIC ® 200 | HCl[1] | Total Water |
|---|---|---|---|---|---|---|---|---|
| 13 | 32.12 | 5.84 | 0.73 | 0.70 | 0.58 | 8.76 | 0.0 | 51.27 |
| 14 | 37.29 | 3.39 | 0.34 | 0.0 | 1.36 | 10.17 | 0.0 | 47.46 |
| 15 | 37.29 | 6.78 | 0.34 | 0.0 | 1.36 | 10.17 | 0.0 | 44.07 |
| 16 | 37.29 | 6.78 | 0.34 | 0.91 | 0.0 | 10.17 | 0.0 | 44.52 |
| 17 | 23.84 | 4.33 | 0.33 | 0.58 | 0.0 | 6.50 | 0.0 | 64.42 |
| 18 | 36.78 | 3.34 | 0.50 | 0.0 | 1.34 | 10.03 | 0.12 | 47.88 |
| 19 | 36.78 | 6.69 | 0.50 | 0.0 | 1.34 | 10.03 | 0.12 | 44.54 |

[1]HCl is added to the aqueous solution before the water-immiscible solution is added.

EXAMPLE 3

Preparation of pH-sensitive microcapsule compositions containing MONDUR®MRS in the capsule wall A mixture of pendimethalin (110.0 g), trimesoyl chloride (1.0 g), MONDUR®MRS, a 4,4'-diphenyl diisocyanate polymer, Mobay Corp., Pittsburgh, Pa. (7.5 g) and AROMATIC® (30 g) is stirred at 50° C. to obtain a water-immiscible solution. The water-immiscible solution is added with stirring to a polyvinyl alcohol solution (120.0 g of a 2 wt/wt % solution) at 50° C. to obtain an emulsion. Thereafter, the stirrer speed is reduced and a solution of 1,6-hexamethylenediamine (0.44 g of a 50 wt/wt % solution), sodium hydroxide (0.36 g of a 50 wt/wt % solution) and water (20.0 g) is added to the stirred emulsion and the resultant mixture is stirred at 50° C. for about 3 hours to form the pH-sensitive microcapsule composition identified as composition number 20 in Table III.

Using essentially the same procedure, the pH-sensitive microcapsule compositions identified as composition numbers 21–27 in Table III are obtained.

TABLE III pH-Sensitive Microcapsule Compositions Containing MONDUR ® MRS

Ingredient/wt/wt %

| Comp. No. | Pendimethalin | MONDUR ® MRS | Trimesoyl Chloride | HMDA | NaOH | Emulsifier[1] | AROMATIC ® 200 | Total Water |
|---|---|---|---|---|---|---|---|---|
| 20 | 38.02 | 2.59 | 0.35 | 0.08 | 0.06 | a/0.83 | 10.37 | 47.70 |
| 21 | 37.79 | 2.58 | 0.69 | 0.15 | 0.12 | a/0.82 | 10.31 | 47.54 |
| 22 | 37.56 | 2.56 | 1.02 | 0.23 | 0.18 | a/0.82 | 10.24 | 47.39 |
| 23 | 37.33 | 2.54 | 1.36 | 0.30 | 0.24 | a/0.81 | 10.18 | 47.23 |
| 24 | 37.92 | 2.59 | 0.34 | 0.15 | 0.12 | b/0.83 | 10.34 | 47.71 |
| 25 | 37.58 | 2.56 | 0.68 | 0.30 | 0.25 | b/0.82 | 10.25 | 47.56 |
| 26 | 31.86 | 2.17 | 0.87 | 0.38 | 0.31 | b/0.70 | 8.69 | 55.02 |
| 27 | 27.58 | 1.88 | 1.00 | 0.44 | 0.36 | b/0.60 | 7.52 | 60.62 |

[1](a) polyvinyl alcohol, (b) GANEX ® P-904, an alkylated vinylpyrrolidone polymer, GAF Corp., Wayne, NJ.

EXAMPLE 4

Preparation of pH-sensitive microcapsule compositions using salts prior to microcapsule formation A mixture of sodium chloride (30.0 g), REAX®88B, sodium salt of lignosulfonic acid, Westvaco, Charleston Heights, S.C. (4.27 g) and water (146.0 g) is adjusted to pH 7 with hydrochloric acid (2.36 g of a 10 wt/wt % solution), and stirred at 60° C. to obtain an aqueous solution. A water-immiscible solution (previously prepared by heating a mixture of pendimethalin (110.0 g), trimesoyl chloride (5.0 g) and AROMATIC®200 (30 g) to 60° C.) is added to the aqueous solution with stirring to obtain an emulsion. Thereafter, the stirrer speed is reduced and a solution of 1,6-hexamethylenediamine (3.28 g of a 50 wt/wt % solution), sodium hydroxide (1.80 g of a 50 wt/wt % solution) and water (20.0 g) is added to the stirred emulsion and the resultant mixture is stirred at 60° C. for about 3 hours to form the pH-sensitive microcapsule composition identified as composition number 28 in Table IV.

Using essentially the same procedure, the pH-sensitive microcapsule compositions identified as composition numbers 29–31 in Table IV are obtained.

TABLE IV pH-Sensitive Microcapsule Compositions Prepared With Salts

Ingredient/wt/wt %

| Comp. No. | Pendi-methalin | NaCl | Trimesoyl Chloride | HMDA | REAX® 88B | NaOH | HCl | AROMATIC® 200 | Total Water |
|---|---|---|---|---|---|---|---|---|---|
| 28 | 30.33 | 8.27 | 1.38 | 0.45 | 1.18 | 0.25 | 0.07 | 11.03 | 47.05 |
| 29 | 38.61 | 8.27 | 1.38 | 0.45 | 1.18 | 0.25 | 0.06 | 2.76 | 47.04 |
| 30 | 19.95 | 12.70 | 1.00 | 0.22 | 1.55 | 0.18 | 0.12 | 5.44 | 58.84 |
| 31 | 37.27 | 9.32 | 1.33 | 0.44 | 1.14 | 0.24 | 0.06 | 2.66 | 47.55 |

EXAMPLE 5

Preparation of pH-sensitive microcapsule compositions using REAX®88B as the emulsifier A mixture of REAX®88B (4.27 g) and water (146.0 g) is adjusted to pH 7 with hydrochloric acid (2.48 g of a 10 wt/wt % solution), and stirred at 60° C. to obtain an aqueous solution. A water-immiscible solution (previously prepared by heating a mixture of pendimethalin (140.0 g), trimesoyl chloride (5.0 g) and AROMATIC®200 (10 g) to 60° C.) is added to the aqueous solution with stirring to obtain an emulsion. Thereafter, the stirrer speed is reduced and a solution of 1,6-hexamethylenediamine (3.28 g of a 50 wt/wt % solution), sodium hydroxide (1.80 g of a 50 wt/wt % solution) and water (20.0 g) is added to the stirred emulsion and the resultant mixture is stirred at 60° C. for about 3 hours to form the pH-sensitive microcapsule composition identified as composition number 32 in Table V.

Using essentially the same procedure, the pH-sensitive microcapsule compositions identified as composition numbers 33 and 34 in Table V are obtained.

TABLE V pH-Sensitive Microcapsule Compositions Prepared With REAX® 88B

Ingredient/wt/wt %

| Comp. No. | Pendi-methalin | Trimesoyl Chloride | HMDA | REAX® 88B | NaOH | HCl | AROMATIC® 200 | Total Water |
|---|---|---|---|---|---|---|---|---|
| 32 | 42.06 | 1.50 | 0.49 | 1.28 | 0.27 | 0.07 | 3.00 | 51.31 |
| 33 | 33.04 | 1.50 | 0.49 | 1.28 | 0.27 | 0.08 | 12.01 | 51.32 |
| 34 | 20.17 | 1.01 | 0.22 | 1.57 | 0.18 | 0.13 | 5.50 | 71.23 |

EXAMPLE 6

Preparation of pH-sensitive microcapsule compositions which contain MONDUR®MRS in the capsule wall and are prepared using salts prior to microcapsule formation A mixture of sodium chloride (20 g), REAX®88B (4.27 g) and water (145.73 g) is adjusted to pH 7 with hydrochloric acid (3.54 g of a 10 wt/wt % solution), and stirred at 60° C. to obtain an aqueous solution. A water-immiscible solution (previously prepared by heating a mixture of pendimethalin (55.0 g), MONDUR®MRS (2.75 g), trimesoyl chloride (2.75 g) and AROMATIC®200 (15 g) to 50° C.) is added to the aqueous solution with stirring to obtain an emulsion. Thereafter, the stirrer speed is reduced and a solution of 1,6-hexamethylenediamine (1.20 g of a 50 wt/wt % solution), sodium hydroxide (0.99 g of a 50 wt/wt % solution) and water (10 g) is added to the stirred emulsion and the resultant mixture is stirred at 50° C. for about 3 hours to form the pH-sensitive microcapsule composition identified as composition number 35 below.

| Composition Number 35 | |
| --- | --- |
| Ingredient | wt/wt % |
| Pendimethalin | 21.05 |
| Sodium Chloride | 7.66 |
| MONDUR ® MRS | 1.05 |
| Trimesoyl Chloride | 1.05 |
| HMDA | 0.23 |
| REAX ® 88B | 1.63 |
| Sodium Hydroxide | 0.19 |
| Hydrogen Chloride | 0.14 |
| AROMATIC ® 200 | 5.74 |
| Total Water | 61.25 |

EXAMPLE 7
Preparation of pH-sensitive microcapsule compositions using dibutyltin dilaurate to catalyze the capsule wall forming reactions A mixture of pendimethalin (110.0 g), trimesoyl chloride (5.5 g), MONDUR®MRS (5.5 g), dibutyltin dilaurate (0.5 g of a 10 wt/wt % solution in AROMATIC®200) and AROMATIC®200 (30 g) is stirred at 50° C. to obtain a water-immiscible solution. The water-immiscible solution is added with stirring to a polyvinyl alcohol solution (130.0 g of a 2 wt/wt % solution) at 50° C. to obtain an emulsion. Thereafter, the stirrer speed is reduced and a solution of 1,6-hexamethylenediamine (HMDA, 2.4 g of a 50 wt/wt % solution), sodium hydroxide (1.98 g of a 50 wt/wt % solution) and water (14.12 g) is added to the stirred emulsion and the resultant mixture is stirred at 50° C. for about 3 hours to form the pH-sensitive microcapsule composition identified as composition number 36 in Table VI.

Using essentially the same procedure, but varying the amount of 1,6-hexamethylenediamine used, the pH-sensitive microcapsule compositions identified as composition numbers 37–39 in Table VI are obtained.

obtain an emulsion. Thereafter, the stirrer speed is reduced and a solution of 1,6-hexamethylenediamine (1.20 g of a 50 wt/wt % solution), sodium hydroxide (0.99 g of a 50 wt/wt % solution), and water (40.0 g) is added to the stirred emulsion and the resultant mixture is stirred at 50° C. for about 3 hours to form the pH-sensitive microcapsule composition identified as composition number 40 below.

| Composition Number 40 | |
| --- | --- |
| Ingredient | wt/wt % |
| Pendimethalin | 19.94 |
| SPAN ® 80 | 0.10 |
| MONDUR ® MRS | 1.00 |
| Trimesoyl Chloride | 1.00 |
| HMDA | 0.22 |
| REAX ® 88B | 1.55 |
| Sodium Hydroxide | 0.18 |
| Hydrogen Chloride | 0.13 |
| AROMATIC ® 200 | 5.44 |
| Total Water | 70.45 |

Using essentially the same procedure, but adding sodium chloride to the aqueous solution, the pH-sensitive microcapsule composition identified below as composition number 41 is obtained.

| Composition Number 41 | |
| --- | --- |
| Ingredient | wt/wt % |
| Pendimethalin | 19.58 |
| Sodium Chloride | 12.46 |
| SPAN ® 80 | 0.10 |
| MONDUR ® MRS | 0.98 |
| Trimesoyl Chloride | 0.98 |
| HMDA | 0.21 |

TABLE VI pH-Sensitive Microcapsule Compositions Prepared Using Dibutyltin Dilaurate Ingredient/wt/wt %

| Comp. No. | Pendi- methalin | MONDUR ® MRS | Dibutyltin Dilaurate | Trimesoyl Chloride | HMDA | NaOH | Polyvinyl Alcohol | AROMATIC ® 200 | Total Water |
| --- | --- | --- | --- | --- | --- | --- | --- | --- | --- |
| 36 | 36.67 | 1.83 | 0.02 | 1.83 | 0.40 | 0.33 | 0.87 | 10.15 | 47.90 |
| 37 | 36.67 | 1.83 | 0.02 | 1.83 | 0.60 | 0.33 | 0.87 | 10.15 | 47.70 |
| 38 | 36.67 | 1.83 | 0.02 | 1.83 | 0.80 | 0.33 | 0.87 | 10.15 | 47.50 |
| 39 | 36.67 | 1.83 | 0.02 | 1.83 | 1.20 | 0.33 | 0.87 | 10.15 | 47.10 |

EXAMPLE 8
Preparation of pH-sensitive microcapsule compositions containing SPAN®80

A mixture of REAX®88B (4.27 g) and water (150.0 g) is adjusted to pH 7 with hydrochloric acid (3.56 g of a 10 wt/wt % solution), and stirred at 60° C. to obtain an aqueous solution. A water-immiscible solution (previously prepared by heating a mixture of pendimethalin (55.0 g), MONDUR®MRS (2.75 g), trimesoyl chloride (2.75 g), SPAN®080, a sorbitan monooleate, ICI Americas Inc., Wilmington, Del. (0.28 g) and AROMATIC®200 (15.0 g) to 50° C.) is added to the aqueous solution with stirring to -continued

| Composition Number 41 | |
| --- | --- |
| Ingredient | wt/wt % |
| REAX ® 88B | 1.52 |
| Sodium Hydroxide | 0.18 |
| Hydrogen Chloride | 0.13 |
| AROMATIC ® 200 | 5.34 |
| Total Water | 58.52 |

EXAMPLE 9
Preparation of pH-sensitive microcapsule concentrate compositions

Sodium chloride (26.24 g) is added to 165.0 g of composition number 32 (from Example 5) with stirring to form the pH-sensitive microcapsule concentrate composition identified as composition number 42 in Table VII.

Using essentially the same procedure, but adding 11.24 g of sodium chloride to 170.0 g of composition number 28 (from Example 4), the pH-sensitive microcapsule concentrate composition identified as composition number 43 in Table VII is obtained.

initial amount of pendimethalin in the microcapsule compositions (0.0100 g) and the percent pendimethalin in the samples.

Figure 1:
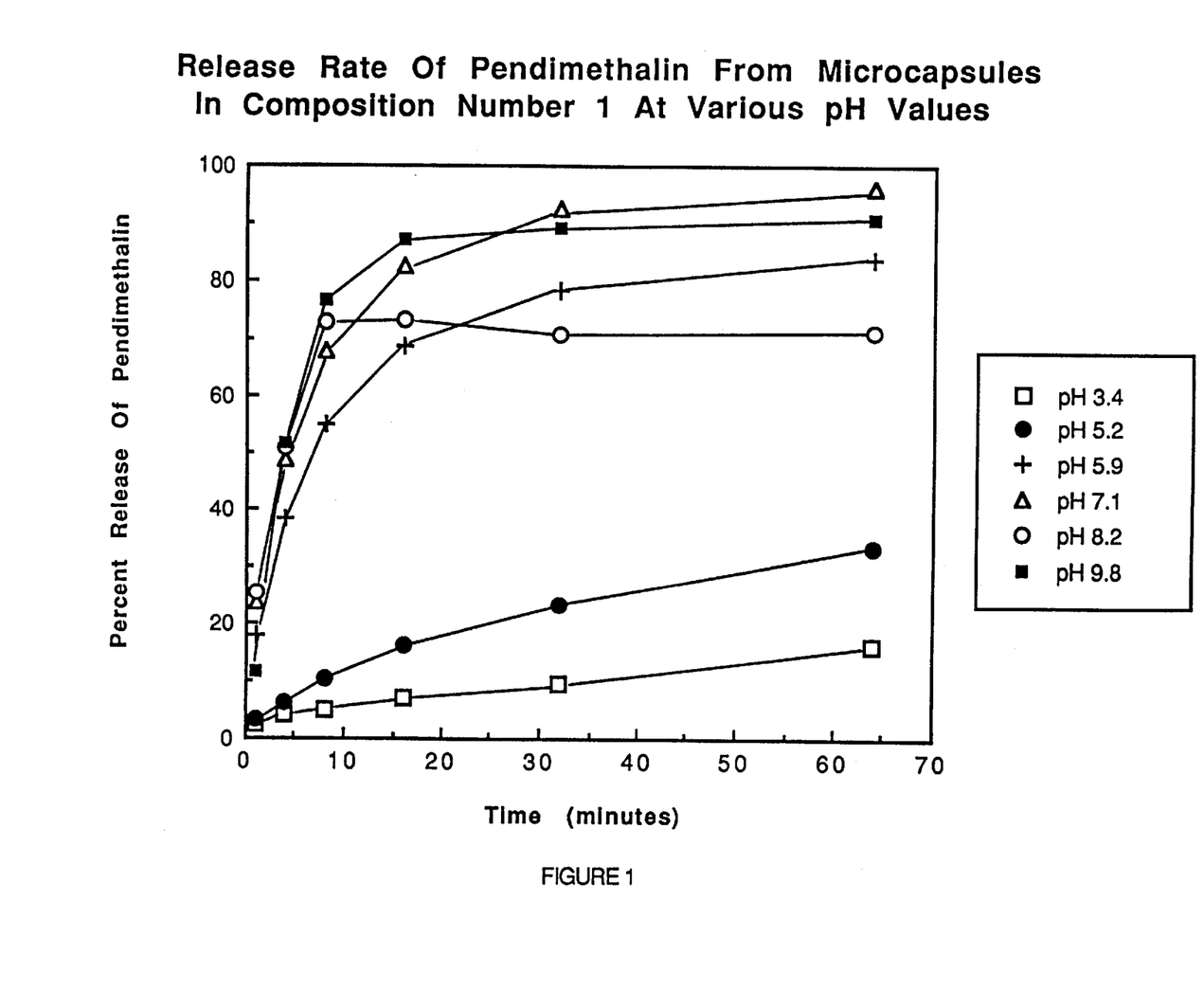
FIG. 1 is a graph depicting the effect of pH on the release of pendimethalin from the microcapsules in composition number 1.

FIG. 1 shows the percent release of pendimethalin from the microcapsules in composition number 1 at several pH values. As can be seen from the data in FIG. 1, the microcapsules are stable at low pH values, and that pendimethalin release increases dramatically at pH values $\geq 5.9$.

Figure 2:
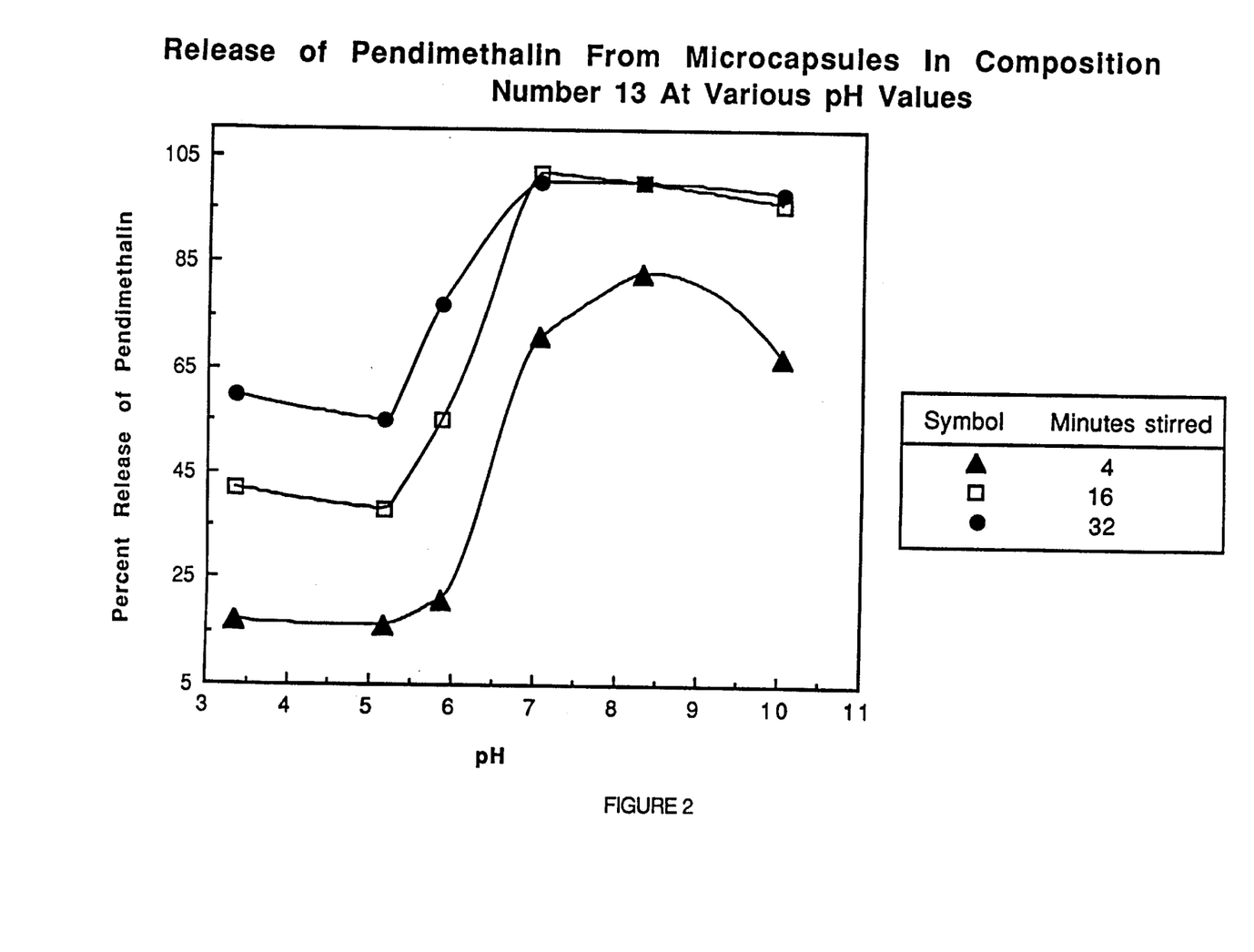
FIG. 2 is a graph depicting the effect of pH on the release of pendimethalin from the microcapsules in composition number 13 at several time intervals.

FIG. 2 shows the percent release of pendimethalin from the microcapsules in composition number 13 at several pH values and time intervals. As can be seen from the data in FIG. 2, the microcapsules are significantly more stable at

TABLE VII pH-Sensitive Microcapsule Concentrate Compositions

| | Ingredient/wt/wt % | | | | | | | |
|---|---|---|---|---|---|---|---|---|
| Comp. No. | Pendi- methalin | NaCl | Trimesoyl Chloride | HMDA | REAX ® 88B | NaOH | HCl | AROMATIC ® 200 | Total Water |
| 42 | 36.29 | 13.72 | 1.30 | 0.42 | 1.10 | 0.24 | 0.06 | 2.59 | 44.27 |
| 43 | 28.45 | 13.96 | 1.29 | 0.42 | 1.11 | 0.23 | 0.07 | 10.35 | 44.13 |

EXAMPLE 10
Evaluation of pH-sensitivities of microcapsule compositions
Buffer solution preparation Various amounts of buffer solution concentrates are added to 100 mL, of a 30 vol/vol % isopropanol solution to obtain the buffer solutions shown below.

| Buffer Solution Concentrate | Grams of Concentrate Added |
|---|---|
| Glacial Acetic Acid | 0.50 |
| Glacial Acetic Acid + | 0.50 |
| 50 wt/wt % NaOH Solution | 0.35 |
| Glacial Acetic Acid + | 2.50 |
| 50 wt/wt % NaOH Solution | 2.85 |
| $KH_2PO_4$ + | 1.00 |
| 50 wt/wt % NaOH Solution | 0.20 |
| $K_2HPO_4$ + | 1.00 |
| $KH_2PO_4$ | 0.10 |
| Boric Acid + | 0.30 |
| 50 wt/wt % NaOH Solution | 0.20 | pH-Sensitivity evaluation

One gram of the appropriate microcapsule composition containing pendimethalin is diluted to 20.00 g with deionized water. An amount of the resultant dispersion which contains 0.0100 g of pendimethalin (as calculated from the initial wt/wt % of pendimethalin in the microcapsule composition) is placed in a 200 mL glass jar. One hundred milliliters of the appropriate buffer solution is added to the jar, the resultant dispersion is stirred at low speed and the pH of the dispersion is measured. At time intervals of 4, 16 and/or 32 minutes, a 3 mL sample of the dispersion is drawn into a 10 mL syringe and expelled through a Teflon Millipore filter into a cuvette. The absorbance of the solution in the cuvette is measured at 400 nm.

A standard calibration curve of wt/wt % pendimethalin vs. absorbance is prepared using dilute solutions of pendimethalin in 30 vol/vol % isopropanol solutions.

The percent pendimethalin in the samples is determined using the standard calibration curve and the samples' absorbance at 400 nm. The percent release of pendimethalin from the microcapsule compositions is then calculated from the low pH values, and that pendimethalin release increases dramatically at pH values >5.9.

Figure 3:
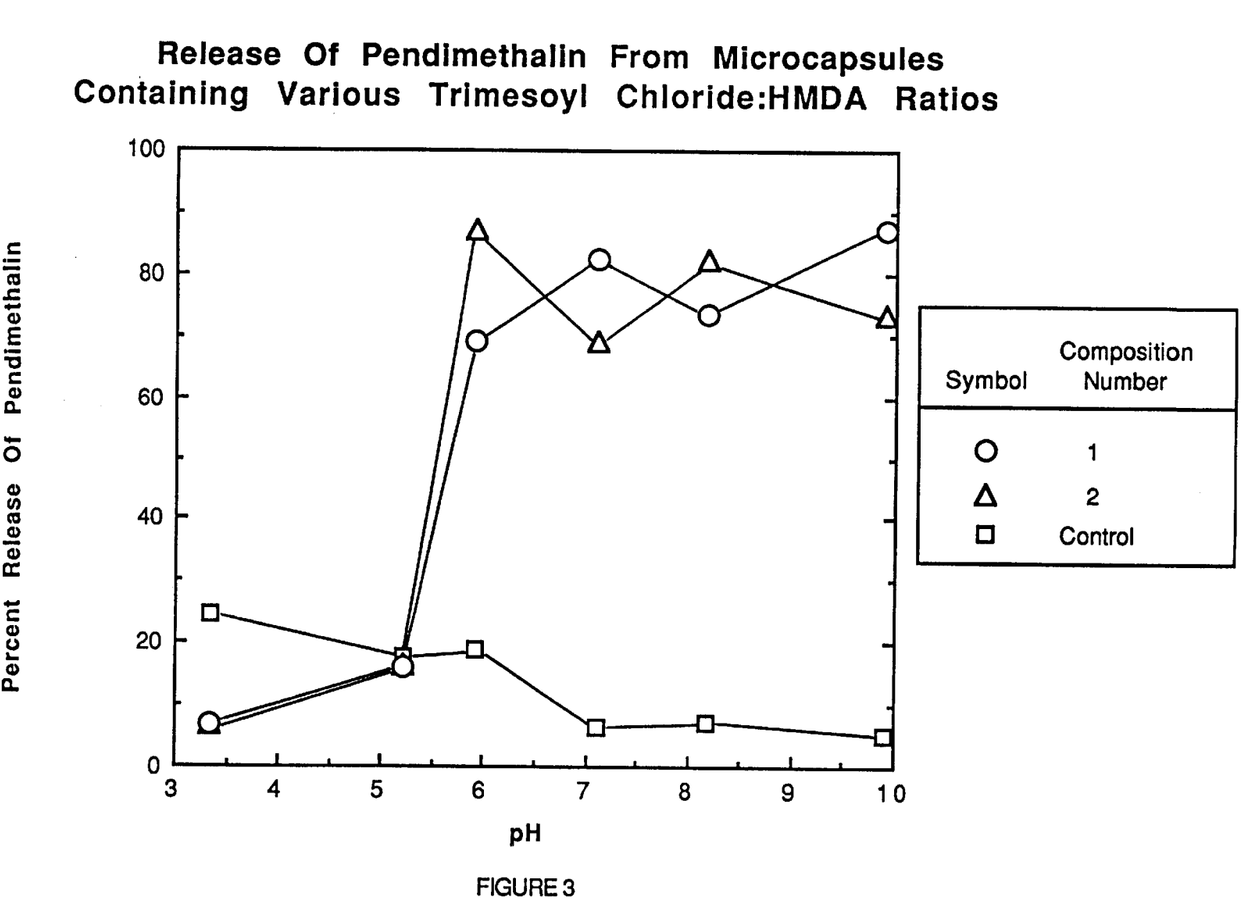
FIG. 3 is a graph depicting the effect of pH on the release of pendimethalin from microcapsules having different trimesoyl chloride:1,6-hexamethylenediamine ratios.

FIG. 3 shows the percent release of pendimethalin from the microcapsules in composition numbers 1 and 2, and the control composition identified below, after stirring in the appropriate buffer solution for 16 minutes.

As can be seen from the data in FIG. 3, microcapsule composition numbers 1 and 2, which have trimesoyl chloride:HMDA ratios of 3:1 and 2:1, respectively, demonstrate desirable pH-sensitivities. In contrast, the control microcapsule composition, which has a trimesoyl chloride:HMDA ratio of 0.5:1, does not demonstrate any desirable pH-sensitivity.

| Control Composition[1] | |
|---|---|
| Ingredient | wt/wt % |
| Pendimethalin | 22.22 |
| Trimesoyl Chloride | 1.59 |
| HMDA | 2.09 |
| Sodium Hydroxide | 0.29 |
| Polyvinyl Alcohol | 0.76 |
| AROMATIC ® 200 | 26.98 |
| Total Water | 46.07 |

[1]The control composition is prepared according to the procedure of Example 1.

EXAMPLE 11
Evaluation of crystal growth

In this evaluation, samples of the appropriate microcapsule compositions (about 30 g) are poured into glass bottles and the bottles are placed in a test chamber. The samples are subjected to temperature cycles of 0°–40° C. and each cycle takes about 24 hours. After several weeks, the samples are removed and crystal growth is evaluated by optical microscopy. The results are summarized in Table VIII. Data in Table VIII is reported by the composition number given in Table IV. The control composition is identified below.

As can be seen from the data in Table VIII, the pH-sensitive microcapsule composition of the present invention does not readily crystallize.

| Control Composition | |
|---|---|
| Ingredient | wt/wt % |
| Pendimethalin | 42.17 |
| MONDUR ® MRS | 0.52 |
| HMDA | 0.09 |
| Sodium Chloride | 10.54 |
| 10% Hydrochloric Acid | 0.07 |
| REAX ® 88B | 1.29 |
| Water | 45.31 |

TABLE VIII

Crystal Growth Evaluation

| Composition Number | Cycle Time (Weeks) | Crystal Growth Observation |
|---|---|---|
| 31 | 4 | no crystals |
| Control | 4 | many crystals |

What is claimed is:

1. An improved process to make aqueous microcapsules containing a water-immiscible active ingredient having a polyamide, polyester or polyamide/polyester shell wall, the improvement which comprises incorporating free carboxylic acid groups in said shell wall by adding excess polyacid halide during shell wall formation by:

(a) providing an aqueous solution comprising an emulsifier;

(b) dispersing, with agitation, in the aqueous solution, a water-immiscible solution comprising a polyacid halide and a water-immiscible active ingredient to form an emulsion; and (c) adding, with agitation, to the emulsion of step (b), a polyamine, a polyol or a mixture thereof, provided that the ratio of acid halide groups to amino and/or hydroxy groups is about 2:1 to less than about 5:1 and further provided that said shell wall formation occurs essentially in the absence of a diisocyanate, a polyisocyanate, a diisocyanate prepolymer or a polyisocyanate prepolymer.

2. The process according to claim 1 wherein a base is added to step (c) in an amount less than one equivalent relative to the acid halide groups.

3. The process according to claim 1 wherein the ratio is about 2:1 to 3:1.

4. The process according to claim 1 wherein the composition has a pH of about pH 2 to pH 4.

5. The process according to claim 1 wherein the aqueous solution comprises about 0.5% to 5% by weight of the emulsifier.

6. The process according to claim 1 wherein the water-immiscible solution further comprises a water-immiscible solvent.

7. The process according to claim 1 wherein the active ingredient is selected from the group consisting of a herbicide, an insecticide, an acaricide, a nematicide, a fungicide and a molluscicide.

8. An improved process to make aqueous microcapsules containing pendimethalin having a polyamide, polyester or polyamide/polyester shell wall, the improvement which comprises incorporating free carboxylic acid groups in said shell wall by adding excess polyacid halide during shell wall formation by:

(a) providing an aqueous solution comprising an emulsifier;

(b) dispersing, with agitation, in the aqueous solution, a water-immiscible solution comprising a polyacid halide and pendimethalin to form an emulsion; and (c) adding, with agitation, to the emulsion of step (b), a polyamine, a polyol or a mixture thereof, provided that the ratio of acid halide groups to amino and/or hydroxy groups is about 2:1 to less than about 5:1.

9. An improved process to make aqueous microcapsules containing water-immiscible active ingredient having a cross-linked amino resin shell wall, the improvement which comprises incorporating free carboxylic acid groups in said shell wall by adding excess polyacid halide during shell wall formation by:

(a) providing an aqueous solution containing an emulsifier;

(b) dispersing, with agitation, in the aqueous solution, a water-immiscible solution comprising a water-immiscible amino resin prepolymer, a polyacid halide and a water-immiscible active ingredient to form an emulsion, provided that the ratio of amino resin prepolymer to polyacid halide is about 20:1 to 5:1 on a weight basis; and (c) heating the emulsion to about 50° C. to 100° C.

10. An improved process to make aqueous microcapsules containing a herbicide having a polyamide, polyester or polyamide/polyester shell wall, the improvement which comprises incorporating free carboxylic acid groups in said shell wall by adding excess polyacid halide during shell wall formation by:

(a) providing an aqueous solution comprising an emulsifier;

(b) dispersing, with agitation, in the aqueous solution, a water-immiscible solution comprising a polyacid halide and a herbicide to form an emulsion; and (c) adding, with agitation, to the emulsion of step (b), a polyamine, a polyol or a mixture thereof, provided that the ratio of acid halide groups to amino and/or hydroxy groups is about 2:1 to less than about 5:1.

* * * * *